United States Patent [19]

Lorenzen et al.

[11] Patent Number: 4,867,153
[45] Date of Patent: Sep. 19, 1989

[54] MEDICAL DRAIN SYSTEM FOR REMOVING LIQUID FROM VENTILATING SYSTEM

[75] Inventors: Rick D. Lorenzen, Ogden; William Houghton, Murray; Darrel Palmer, Sandy; Kevin Kammerer, Park City, all of Utah

[73] Assignee: Ballard Medical Products, Midvale, Utah

[21] Appl. No.: 198,402

[22] Filed: May 24, 1988

[51] Int. Cl.⁴ ............................................. A62B 7/10
[52] U.S. Cl. ............................ 128/205.12; 128/205.24
[58] Field of Search .................... 128/205.12, 206.22, 128/205.19, 205.24

[56] References Cited

U.S. PATENT DOCUMENTS

| | | | |
|---|---|---|---|
| 3,454,005 | 7/1969 | Eubanks et al. | 128/205.12 |
| 4,327,718 | 5/1982 | Cronenberg | 128/205.12 |
| 4,333,451 | 6/1982 | Paluch | 128/205.12 |
| 4,456,008 | 6/1984 | Clawson et al. | 128/205.12 |
| 4,558,696 | 12/1985 | Eiserman et al. | 128/205.12 |

Primary Examiner—Paul T. Sewell
Assistant Examiner—Aaron J. Lewis
Attorney, Agent, or Firm—Lynn G. Foster

[57] ABSTRACT

A gravity drainage system for manual removal of liquid accumulated in ventilating tubing which does not require interruption of ventilation or manual disassembly of drainage of the tubing. Periodic evacuation of accumulated liquid from the drainage system without interruption of ventilation is also facilitated.

11 Claims, 6 Drawing Sheets

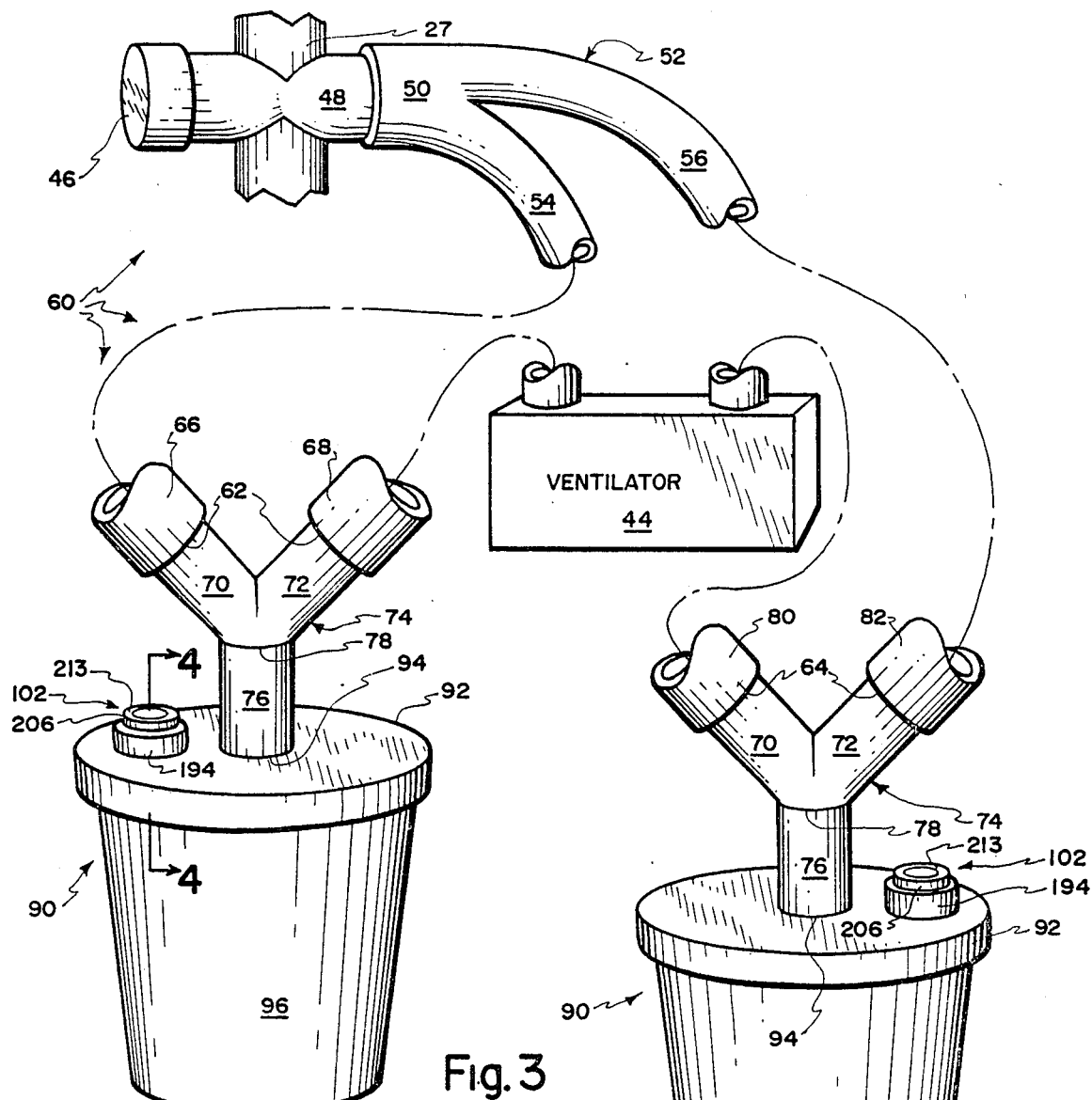
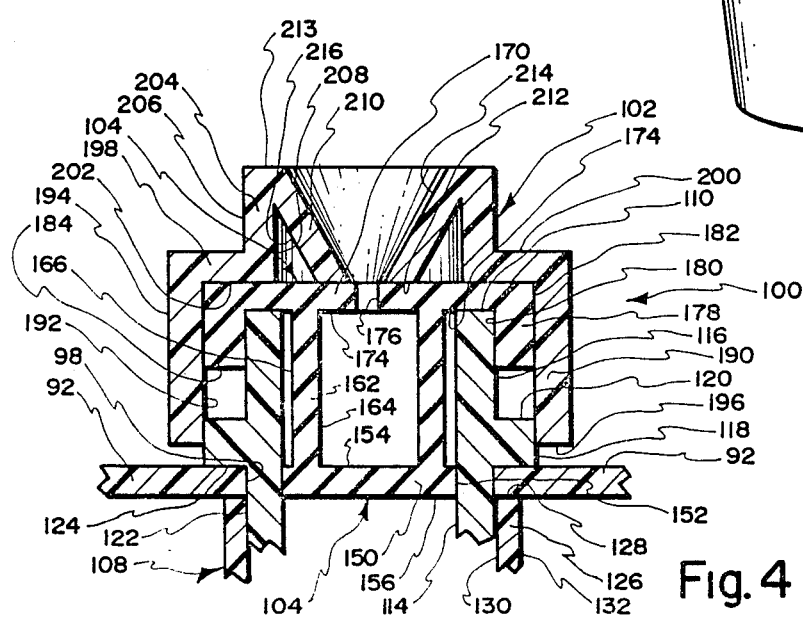
Fig. 3
Fig. 4

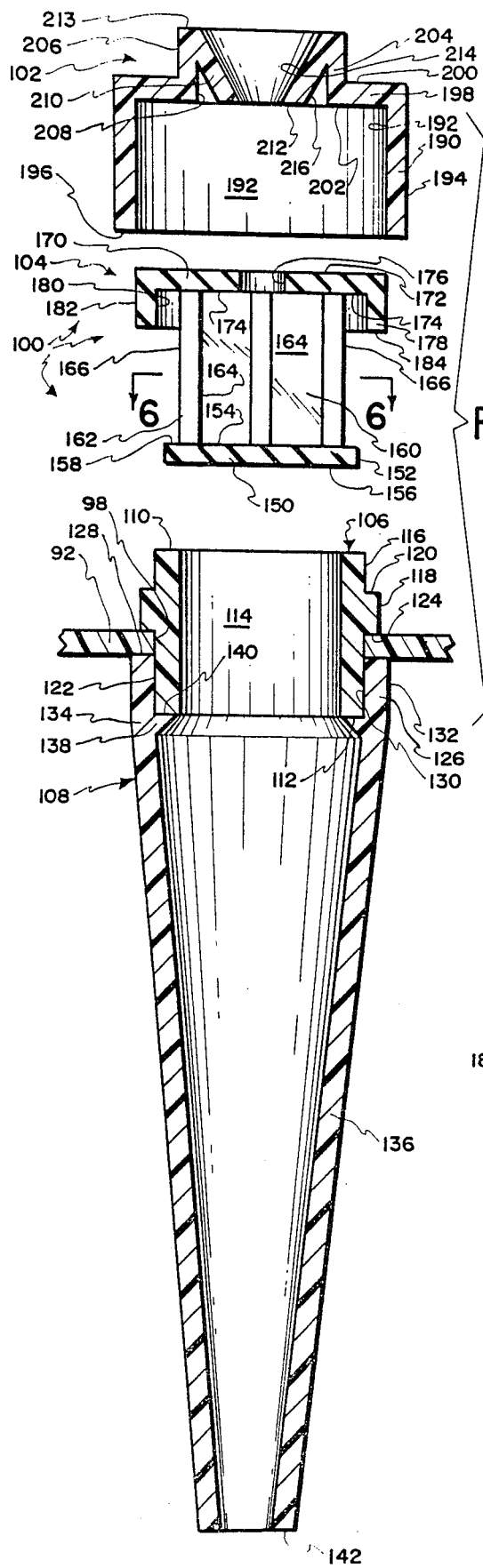
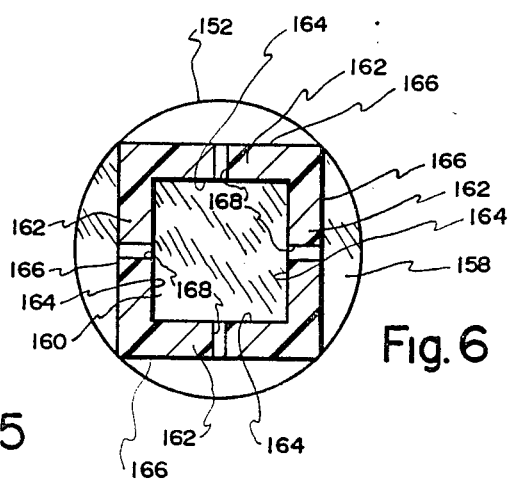
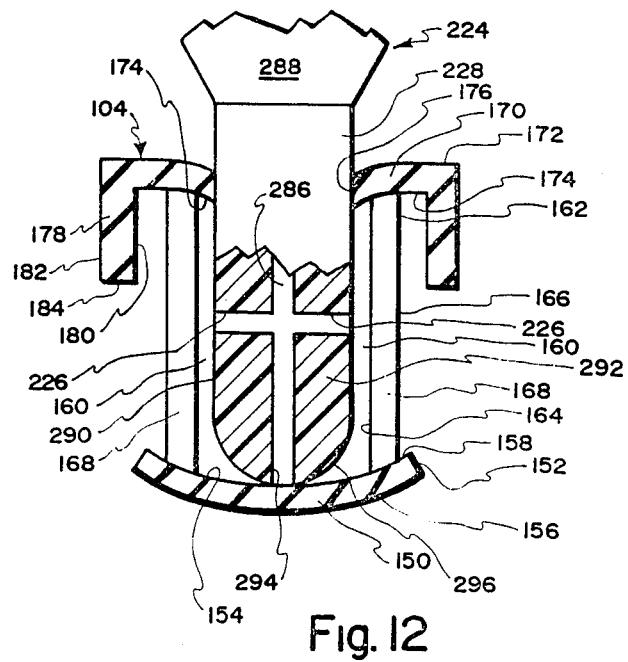
Fig. 5
Fig. 6
Fig. 12

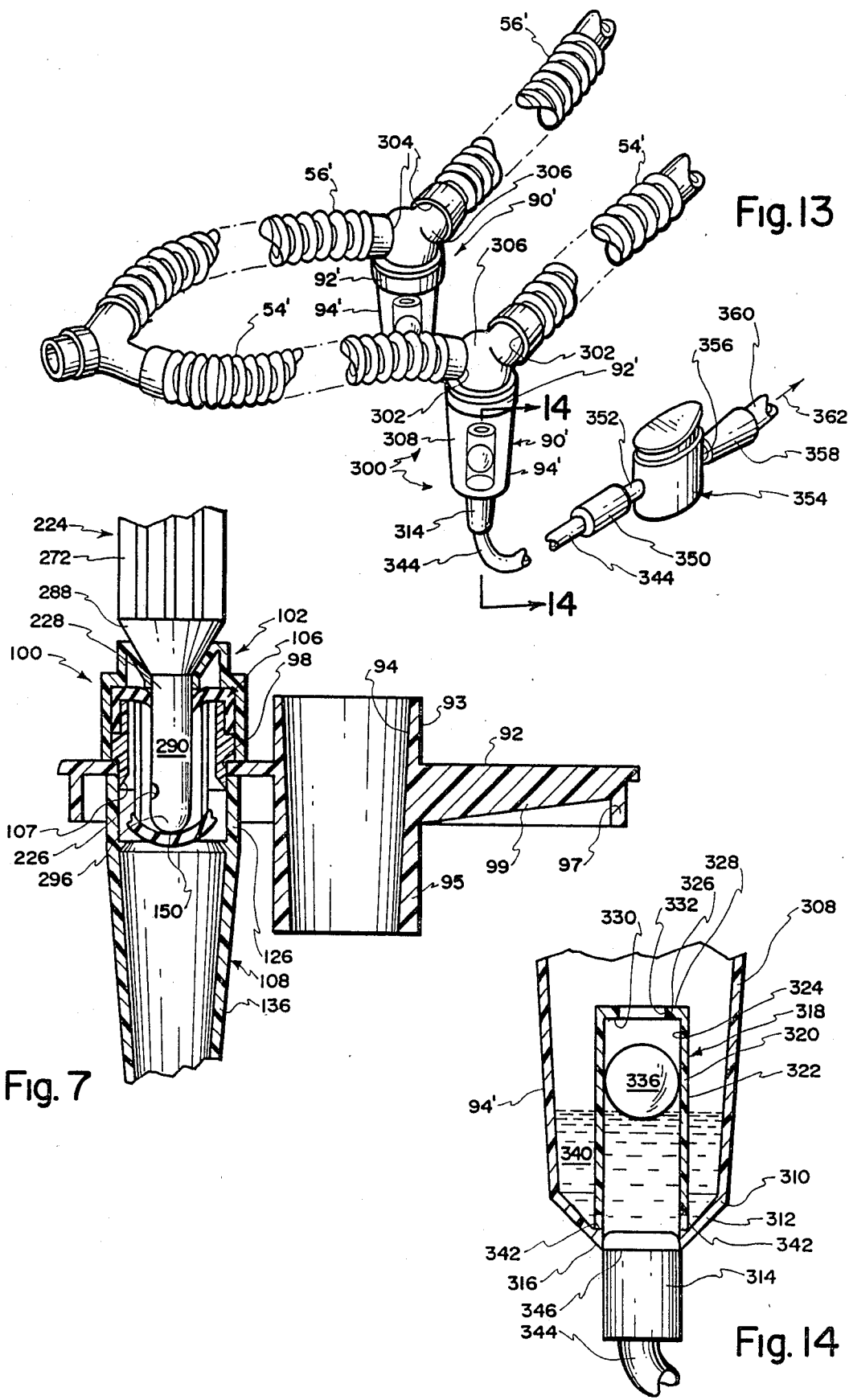

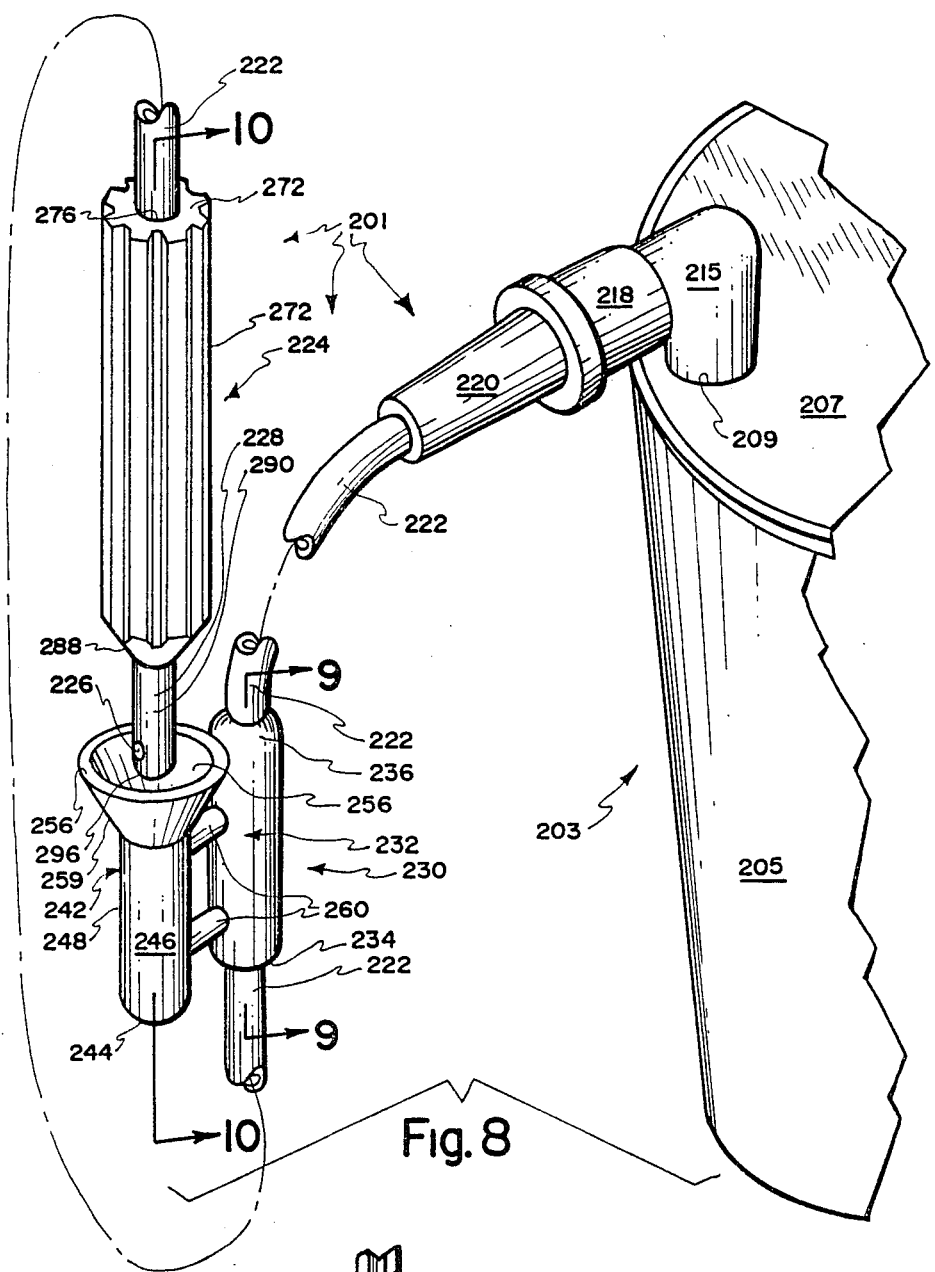
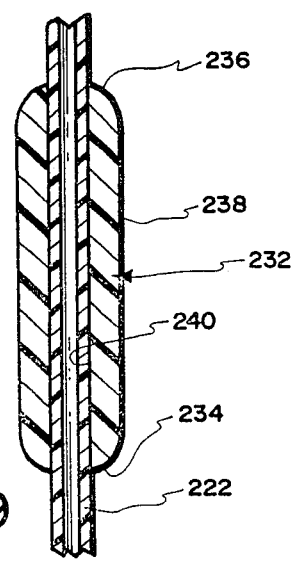
Fig. 8
Fig. 9

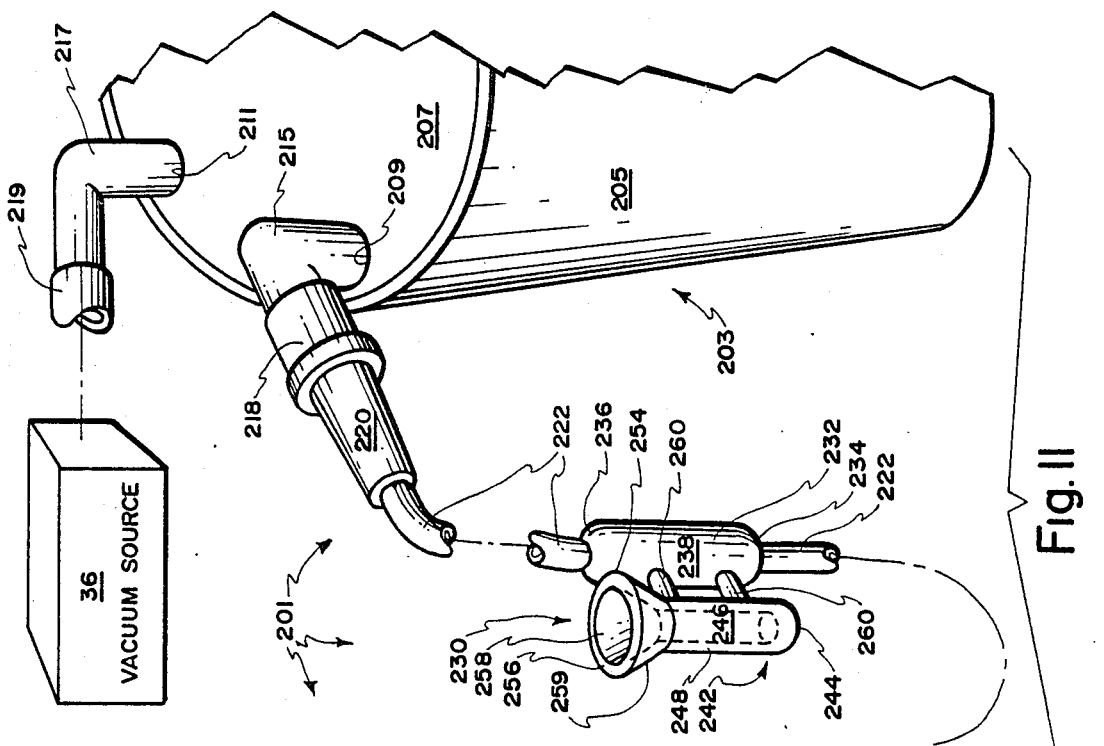
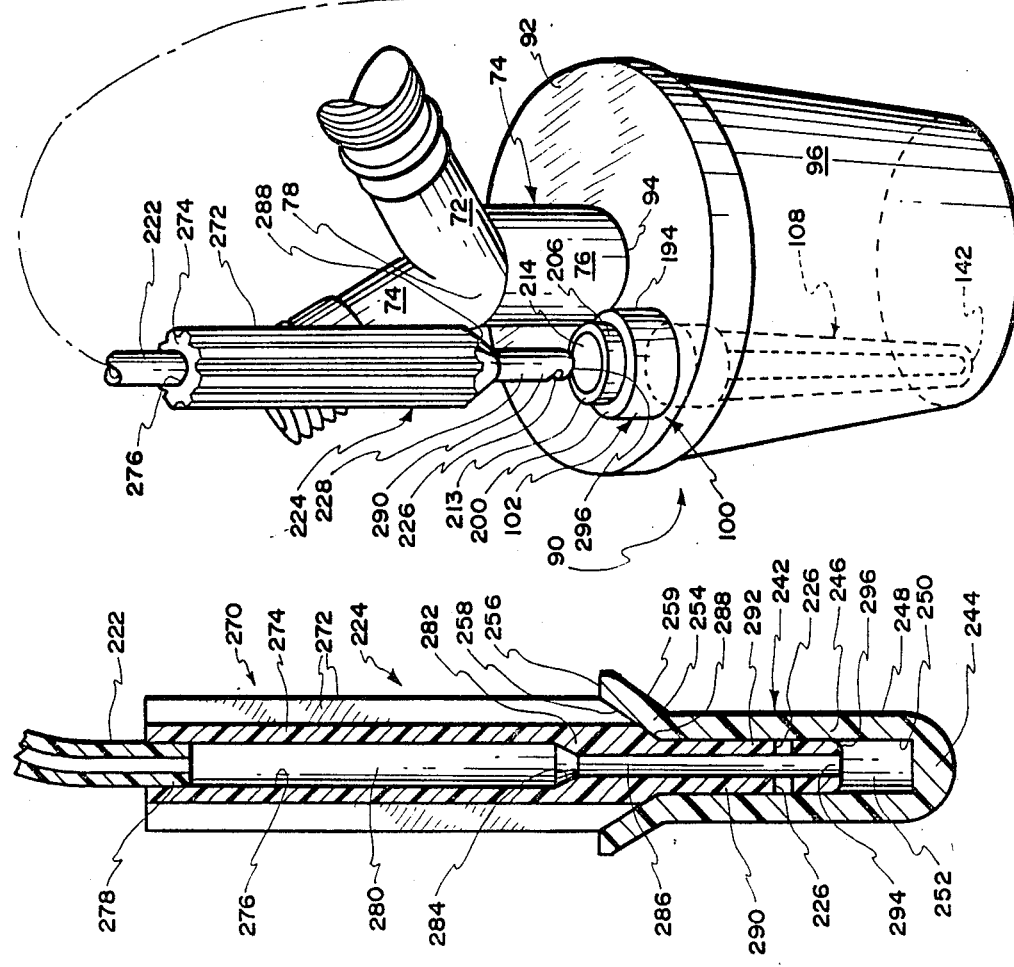

MEDICAL DRAIN SYSTEM FOR REMOVING LIQUID FROM VENTILATING SYSTEM

FIELD OF INVENTION

The present invention relates generally to lung ventilation and, more particularly to a novel drain system for cumulation and removal of liquid condensation produced inside a ventilator circuit.

PRIOR ART

Heretofore, it has been the practice in the medical arts to cumulate condensed liquid in a ventilator circuit in the ventilating tubing thereof. Excessive cumulation of such liquid requires interruption of ventilation and manual drainage of the disconnected ventilating tubing, which risks contamination to medical personnel and patients.

BRIEF SUMMARY AND OBJECTS OF THE INVENTION

In brief summary, the present invention overcomes or substantially alleviates the problems of prior art and comprises a drainage system for manual removal of cumulated liquid in the tubing of a ventilation system for a medical patient without requiring interruption of ventilation or manual drainage of the ventilation system. Closed system periodic evacuation of accumulated ventilation liquid from the drainage system without interruption of ventilation is also facilitated.

With the forgoing in mind, it is a primary object of the present invention to provide a drain system which overcomes or substantially alleviates the problems of the prior art.

It is another important object to provide a novel medical drainage system, and related methods.

A further significant object of the present invention is the provision of a novel closed medical drainage system, including methods, for manually removing liquid accumulated in tubing of a ventilation system for a medical patient without interruption of patient ventilation.

An additional dominant object is the provision of a novel medical ventilation drainage system whereby periodic evacuation of accumulated ventilated liquid is facilely obtained while ventilation continues.

These and other objects and features of the present invention will be apparent from the detailed description taken with reference to the accompanying drawings.

BRIEF DESCRIPTION OF THE DRAWINGS

FIG. 3 is a perspective representation of a drainage system in accordance with the principles of the present invention incorporated into a ventilating system of the type illustrated in FIG. 2;

FIG. 4 is an enlarged fragmentary cross-section taken along lines 4—4 of FIG. 3;

FIG. 5 is an enlarged exploded cross-sectional view of the components forming the assembly of FIG. 4;

FIG. 6 is a cross-sectional view taken along lines 6—6 of FIG. 5;

FIG. 7 is fragmentary cross-section of the assembly of FIG. 4 with an evacuation probe inserted therein;

FIG. 8 is an enlarged fragmentary perspective of an evacuation system by which accumulated moisture in the drainage system of FIG. 3 may be periodically removed;

FIG. 9 is an enlarged cross-sectional view taken along lines 9—9 of FIG. 8;

FIG. 10 is a cross-sectional view taken along lines 10—10, with the proximal probe end of the evacuation tube fully disposed within the storage funnel;

FIG. 11 is a fragmentary enlarged perspective representation showing the evacuation system being joined to the drainage system for evacuation of accumulated moisture;

FIG. 12 is an enlarged fragmentary elevational view showing the proximal end of the evacuation probe fully inserted in the evacuation tube receiving chamber of the drainage system;

FIG. 13 is a fragmentary perspective representation of a second valved drainage system for se in conjunction with a ventilating system for involuntary respiration of a medical patient; and FIG. 14 is an enlarged cross-sectional view taken along lines 14—14 of FIG. 13.

DETAILED DESCRIPTION OF THE ILLUSTRATED EMBODIMENTS

Figure 1:
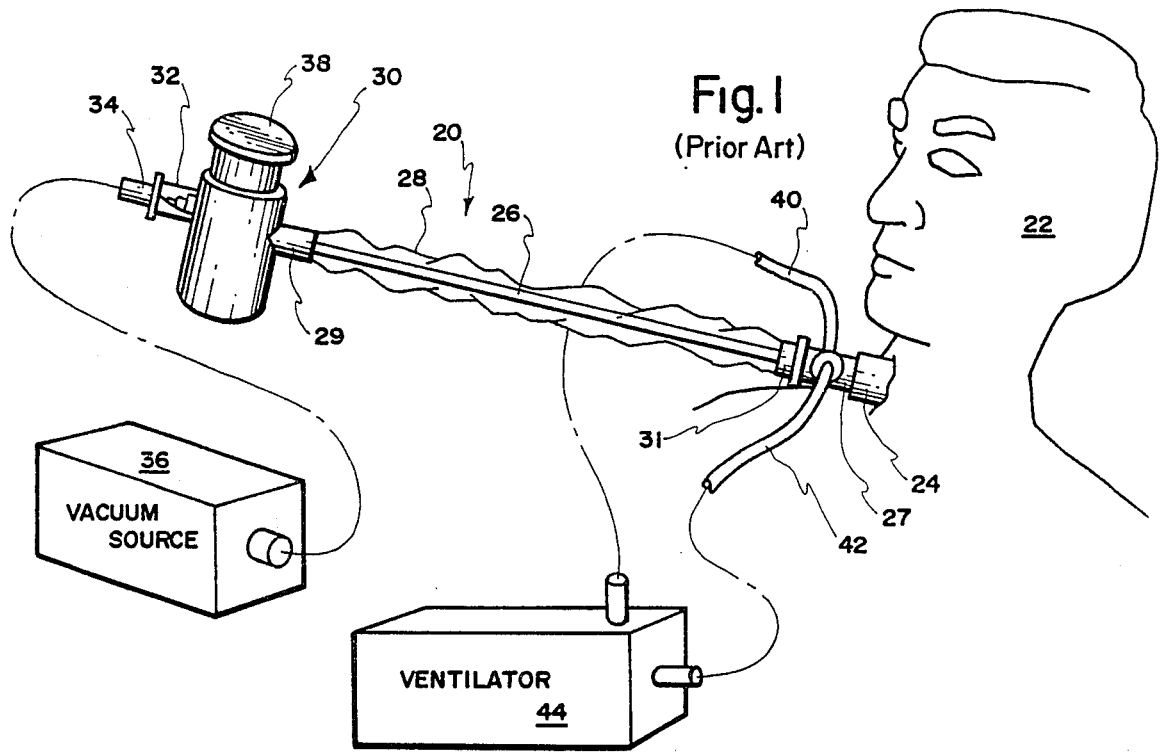
FIG. 1 is a perspective representation of a first prior art ventilating/aspirating system.
Figure 2:
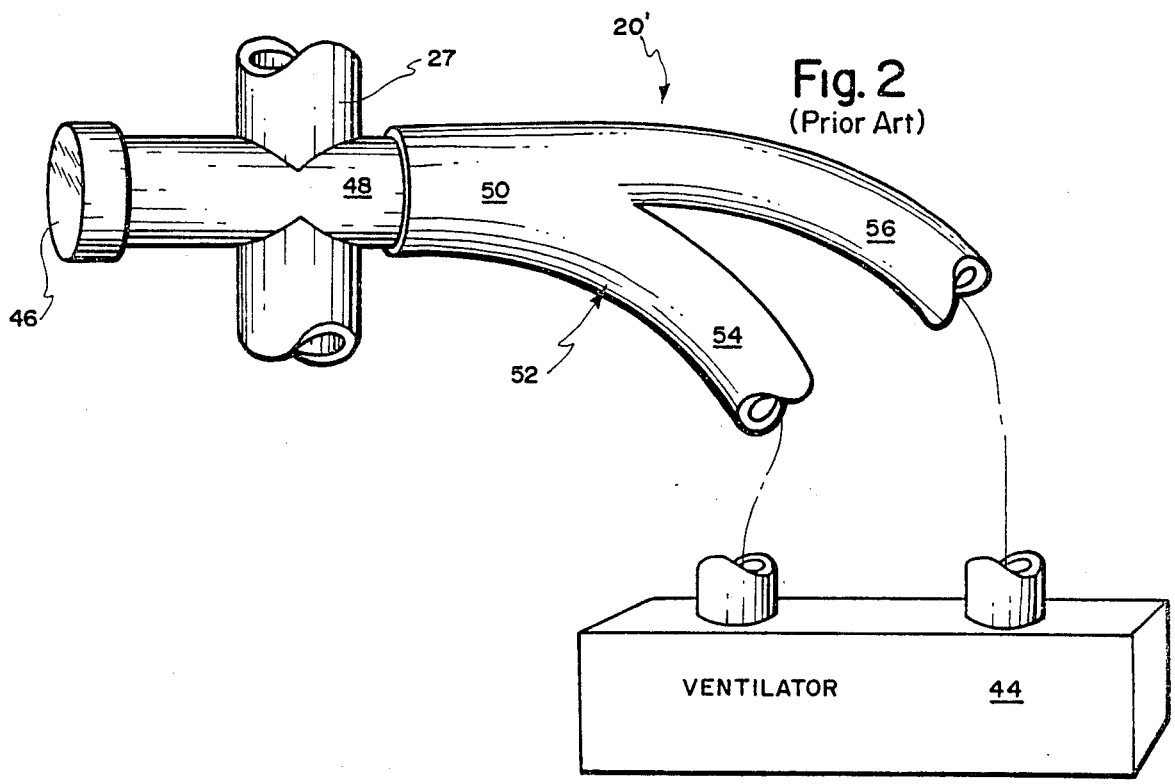
FIG. 2 is large perspective representation of a second prior art ventilating system.

Reference is now made to the drawings wherein like numerals are used to designate like parts throughout. Two state-of-the-art (prior art) ventilator systems are illustrated in FIGS. 1 and 2. The conventional ventilator system of FIG. 1 is generally designated 20. The ventilating system 20 also has an aspirating capability for periodic removal of accumulated secretions from the lungs of the medical patient 22, which is also now conventional. Ventilating mechanism 20, in FIG. 1, is illustrated as being connected to patient 22 at a tracheostomy connector 24 or an endotracheal tube and left indwelling for extended use over a protracted interval of time. The connection to the tracheostomy fitting 24 is via a hollow cross 27. Mechanism 20 comprises a central portion comprising an interior sterile aspirating catheter tube 26 having a hollow interior passageway therethrough of sufficient capacity to aspirate secretions from the lungs of patient 22. The aspirating catheter tube 26 is formed of suitable synthetic resinous material such as medical grade transparent polyvinyl chloride and further comprises an annular wall of essentially uniform thickness throughout. Catheter tube 26 has an outside diameter selected to pass through the fitting 27 and 24, the throat and into the lungs of the patient 22.

Aspirating catheter tube 26 has sufficient strength to prevent buckling, bending, twisting of the catheter tube, which would otherwise occlude or tends to occlude the interior passageway thereof. The tube 26 is surrounded by a sack or flexible envelope 28, formed of suitable impervious synthetic resinous film material of medical grade, such as polyethylene film in sleeve form. One end of the flexible envelope 28 is illustrated as being selectively detachably joined at collar 31 to the cross fitting 27, while the other end is detachably connected at collar 29 to a manually operable, normally closed valve, generally designated 30.

The envelope 28 allows ready manipulation of the catheter tube 26 disposed therein by manually collapsing the envelope 28 against the tube 26 and jointly displacing both a very short distance. This is repeated until the sack has been placed in an accordion condition and tube 26 accurately inserted into the desired lung. The end 32 of the normally closed manual valve 30 is connected by a hollow tube 34 to a conventional vacuum source 36. Thus, when the plunger 38 of the valve 30 is depressed, negative pressure from the vacuum source 36 is applied to the interior passageway of the inserted catheter tube 26 to evacuate secretions accumulated in the lung where the distal tip of the catheter tube has been positioned.

The distal fitting 27 to which the envelope 28 is attached at collar site 31, comprises a hollow cross. Consequently the catheter tube 26 may pass fore and aft through the fitting 27 and influent and effluent ventilating gas is delivered to and removed from the lungs of the patient via hollow tubes 40 and 42, which are in fluid communication with the interior of the fitting 27 and thence with the lungs of the patient 22. The ventilating tubes 40 and 42 are in fluid communication with a standard ventilator 44.

The ventilating system 20 may be that which is disclosed in U.S. Pat. No. 4,569,344, which was granted Feb. 11, 1986 to the assignee of the present application. The contents of U.S. Pat. No. 4,569,344 is incorporated herein by reference.

Prior art ventilating system 20' of FIG. 2 differs from the ventilating system 20 of FIG. 1 only in that one side tube of the cross 27 is capped at 46 to prevent oxygen gas flow therethrough and the other transversely directed tube 48 of the cross-fitting 27 receives end 50 of a hollow Y tubular piece 52 in press-fit relation. Tubular piece 52 is bifurcated and comprises first and second hollow tubes 54 and 56, which are in fluid communication with ventilator 44 so that influent and effluent gas may be communicated to and from the lungs of the patient 22 in a well known and conventional fashion.

In the course of utilization of state-of-the-art ventilating systems, such as those illustrated in FIGS. 1 and 2, there is a substantial accumulation of liquid in the tubes and fittings comprising the ventilator gas flow path. This liquid is derived from moisture present in the lungs of the patient or may consist of residual lavage solution applied to the lungs of the patient or moisture introduced into the ventilating tubes from the ventilator, particularly where the ventilator comprises a humidifier.

In any event, heretofore, no apparatus or methodology has been proposed by which liquid accumulating in a ventilating system of the type in question can be removed without interruption of ventilation. It has been necessary, in order to remove such liquid, to interrupt the ventilation and disconnect and empty the liquid from tubes and fittings forming the ventilation path. This is cumbersome, traumatic to the patient and may endanger the patient's well being under circumstances where a continuous supply of oxygen is essential.

A presently preferred form of the invention, illustrated as being integrated into the ventilating system 20' of FIG. 2, is depicted in FIG. 3. The ventilating/drainage system of FIG. 3 is generally designated 60. Since the ventilating/drainage system 60 includes the ventilating system 20' of FIG. 2, no further description of the components of ventilating system 20' is deemed necessary. Only the differences between the system 60 and the system 20' will be described. The ventilating tubes 54 and 56 are elongated and severed at sites 62 and 64, respectively. The intermediate ends 66 and 68 of the tubing of 54 at severed site 62 are respectively press-fit upon opposed branch lines 70 and 72 of a hollow Y fitting 74 formed of shape-retaining rigid synthetic resinous material. The upwardly-directed opposed hollow arms or branches 70 and 72 of each Y fitting 74 merge with a downwardly-directed hollow arm or branch 76 at site 78.

The intermediate ends 80 and 82 of the ventilating tube 5 adjacent the severance site 64 are connected to a second hollow Y fitting 74 in the aforementioned fashion.

As can be seen schematically from FIG. 3, the two fittings 74 are disposed in the ventilating/drainage system 60 at an elevation below any Other part of the ventilating tube 54 and 56. Consequently, moisture internally present within the ventilating tubes 54 and 56 will drain by force of gravity, on a continuous basis, downwardly to the fittings 74. At the same time, ventilation is continued without interruption, using the ventilator 44 and the ventilating tube 54 and 56.

The downwardly directed hollow branch 76 of each Y fitting 74 is in sealed fluid communication with the hollow interior of a container, generally designated 90. More specifically, the hollow interior of the downwardly directed tubular branch 76 of each Y coupling 74 is in alignment with an aperture 94 in the lid 92 of the associated container 90 and is preferably telescopically connected to the lid at boss 93. See FIG. 7. The hollow branch 76 is thus secured to the lid 92 at site 93/94 in secure, sealed relation, as by bonding. Each container 90 comprises a hollow impervious elongated cup-shaped receptacle 96. If desired, boss 93 can extend downwardly well below the lid 92 to form an internal sleeve 95 (FIG. 7) so that if the container 96 is inadvertently inverted or tipped on its side, there is less likelihood of liquid flow back into the ventilation tubing. Boss 93 and sleeve 95 are illustrated as comprising a wall having a tapered wall thickness which progressively increases in a downward direction. Also, radially directed interior reinforcing ribs 99 integral with the remainder of the lid 92 are presently preferred. See FIG. 7.

The associated lid 92 is force-fit at lip 97 (FIG. 7), in a conventional fashion, upon the upper edge of the associated receptacle 96 to releasibly secure the two parts together in air-tight relation.

Each lid 92 comprises an aperture 98 therein (FIG. 4) into which a probe-receiving assembly, generally designated 100, is fitted in air-tight relation. Adhesive may be used, if desired, to secure the probe-receiving assembly 100 in its inserted relation in lid 92 at aperture 98. The probe-receiving assembly 100 is shown in its normally closed empty position in FIG. 4, which position prevents loss of vacuum pressure from within the interior of the ventilating system 60. It is to be appreciated that each hollow Y fitting 74 accommodates closed gravity drainage directly into the associated container 96, which may be of any desired size. It is preferred that each receptacle 96 be of sufficient size that a substantial quantity of liquid may be accumulated therein over a period of time of about one hour. It is preferred that each container 90, including the associated lid 92 and the receptacle 96, be formed synthetic resinous materials and have sufficient strength to retain their respective shapes under normal conditions of use.

The probe-receiving assembly 100 of each container 90 comprises an exterior cylindrical cap, generally designated 102 and an interiorly hollow probe receptacle, generally designated 104. See FIG. 4. The probe-receiving assembly also comprises a stepped sleeve, generally designated 106, and a tapered evacuation pipe, generally designated 108. See FIG. 5.

The stepped sleeve 106, best shown in FIGS. 4 and 5, has a relatively short axial length and comprises a top edge 110 and a bottom edge 112. The interior of the sleeve 106 is of uniform diameter along interior surface 114. The exterior of the sleeve 106 comprises an annular top surface 116, enlarged annular surface 118, separated from surface 116 by a shoulder 120, and lower reduced diameter annular surface 122, separated from annular surface 118 by radial shoulder 124. The radial shoulder 124 rests on the upper surface of the container lid 92, because the diameter of the surface 118 is greater than the diameter of the lid opening 98.

As shown in FIG. 5, the diameter of the annular surface 122 is substantially the same as the diameter of the lid opening 98 so that a snug fit results. If desired, the sleeve 106 may be permanently located in the position illustrated in FIG. 5 by use of a suitable bonding agent or adhesive. Alternatively, the fit between the surface 122 and the surface forming aperture 98 may be such as to create an interference fit, which not only secures the sleeve 106 in the illustrated position but creates and air-tight seal between the lid 92 and the sleeve 106 at aperture 98. Further, the lid 92 and the sleeve 106 may be injection molded as a single part, as opposed to two parts.

The evacuation pipe 108 is axially aligned with the collar 106 and has an axial length running from the lower surface of the lid 92 to a location immediately above the bottom surface of the receptacle 96, whereby, under force of vacuum, essentially all of the liquid contents of the receptacle 96 may be evacuated without ventilation interruption. The upper end of pipe 108 comprises an annular wall section 126. Wall section 126 terminates at an upper blunt edge 128, which is illustrated as being disposed normal to the axis to the pipe 108. The annular wall section 126 comprises an interior annular surface 130, the diameter of which is substantially the same as the annular surface 122 of the collar 106. Annular wall section 126 also comprises and exterior annular surface 132. Upper annular wall 126 merges along an annular site 134 with a downwardly convergently tapered elongated conical hollow spout 136. Spout 136, at the top thereof, is illustrated as comprising an annular radially inwardly directed shelf 138 comprising an upper shoulder surface 140 against which the lower edge 112 of the sleeve 106 rests. Otherwise, the conical wall 136 is illustrated as being of uniform thickness and uniform taper along the entire length thereof, terminating in a blunt distal edge 142. The pipe 108 and the sleeve 106 may be secured one to the other, as illustrated in FIG. 5, by reliance upon an interference-fit relationship and/or by use of a suitable bonding agent. If desired, annular wall section 126 of the pipe 108 may be secured to the lid 92 adjacent edge 128. In any event, the interface between the collar 106 and the pipe 108 must secure those two parts together to provide an air-tight seal therebetween.

It is presently preferred that the collar 106 and the pipe 108 be formed of shape retaining rigid durable synthetic resinous materials.

The probe receptacle 104 is preferably formed of silicone rubber or like synthetic material and is force-fit inserted into the collar 106 from the upper end to achieve the unstressed assembled position illustrated in FIG. 4. Internal probe-receiving receptacle 104 comprises a disk-shaped flat base wall 150 comprising an annular edge 152 and a uniform thickness defined by upper surface 154 and lower surface 156. Base wall 150 at edge 152, when unstressed, creates an air tight seal against the interior surface 114 of the collar 106. The majority of the surface 154 is internal of the member 104 with a lip portion 158 thereof being disposed at the exterior of the member 104. The member 104 preferably comprises a single piece formed by existing injection molding techniques and comprises a hollow rectangular or square interior probe-receiving chamber 160 defined by four identical side walls 162. Each wall 162 is integral with the other walls 162 and the base wall 150 and is illustrated as being of uniform thickness comprising a flat interior surface 164 and a flat exterior surface 166. Each vertical wall 162 comprises a central open slot 168. When the probe is fully inserted, the member 104 is elongated or stretched forcing the wall 150 at edge 152 downwardly out of sealed relation with the collar wall surface 114. See FIG. 7. This causes the imposition of the negative pressure of the probe through the slots 168 upon the liquid accumulated in the associated receptacle 96. When the probe is removed from the chamber member 104, the memory of the material of member 104 causes the valve disk 150 to reseat in the collar 106 as illustrated in FIG. 4. To aid in facilitating return of the disk 150 to the closed position of FIG. 4, the lower edge of collar 106 may be beveled as illustrated at 107 in FIG. 7.

The upper ends of the four walls 162 merge integrally with a top annular wall 170. Wall 170 comprises an upper flat surface 172 and a lower flat surface 174, part of which is inside and part outside probe-receiving chamber 160. The center of the wall 170 is interrupted by a circular aperture 176, the diameter of which is less than the diameter of the tip of the probe to be inserted into the chamber 160. Thus, the surface 176 and the surface of the probe tip create a seal. The outer radial edge of the wall 170 merges with a downwardly directed annular flange 178, which is illustrated as being of uniform thickness throughout comprising inside annular surface 180 and outside radial surface 182. The wall 178 terminates in a blunt transverse edge 182. The vertical distance of the wall 178 is illustrated as being about 25 percent of the axial length of the interior probe-receiving receptacle 104. The diameter of the surface 180 is selected to be slightly less than the diameter of the annular surface 116 of the collar 106 so that the wall 178 is slightly stretch-fit over the upper end of the collar into the assembled position illustrated in FIG. 4. It is to be appreciated that the interface formed between the surfaces 180 and 116 is air-tight as is the interface between the edge 152 of the wall 150 and the interior surface 114 of the collar 106.

The cap member 102 preferably is formed of rigid synthetic resinous material and comprises an internal annular wall 190 defined by interior surface 192 and exterior surface 194. The wall 190 terminates in a blunt transverse lower edge 196. Annular wall 190 merges integrally with a radially-directed wall 198, which comprises upper annular exposed surface 200 and an inner annular surface 202. In effect, the wall 198 inwardly steps the exterior of the cap member !02. with the wall 198 integrally merging with an axially directed annular wall 204, which is substantially diametrically reduced in respect to wall 190.

Annular upper wall 204 is illustrated as being of uniform thickness and comprises an exterior annular surface 206 and an inner annular surface 208. Wall 204 integrally merges adjacent its upper blunt edge 213 with a downwardly directed converging frusto-conical wall 210. Wall 110 terminates in a beveled annular edge 212 disposed in a horizontal plane and comprises exterior and interior walls 214 and 216, respectively.

The diametral size of the wall 204 substantially corresponds to the size of the probe-receiving chamber 160. The maximum diametral size of the edge 212 is slightly greater than the aperture 176, as illustrated best in FIG. 4. The diameter of the surface 192 is substantially the same as the diameter of the wall surface 182 of member 104 when in its assembled condition, illustrated in FIG. 4. Accordingly, surface 192 is sealingly contiguous with surface 182 in the assembled condition as illustrated in FIG. 4. The axial length of wall 190 is illustrated as being such that it contacts the top surface of the container lid 92. In the assembled state shown in FIG. 4, the probe-receiving assembly 100 is at rest and is illustrated as being sealed against the aperture 98 of the container lid 92 in air-tight relation. In this condition the probe-receiving assembly 100 is ready to receive the distal tip of an evacuating probe, as illustrated in FIG. 10.

Reference is now made to FIGS. 8 through 11, which illustrate a presently preferred closed liquid evacuation system for periodic removal of liquid accumulated in a drain system made and practiced in accordance with the present invention. For example, the evacuation system, which is generally designated 201 in FIGS. 8 through 11 may be used to remove from time to time liquid accumulating in all containers 90 of a ventilation/drainage system.

The evacuation system 201, shown in FIGS. 8 and 11, comprises a vacuum source, which may comprise the previously mentioned conventional vacuum source 36, usually a hospital suction system, and a large capacity liquid-storage bucket 203 comprising a large volume lower receptacle 205 and a press-fit lid 207, both of well known conventional design. The lid 207 is interrupted by two apertures 209 and 211, each of which receives in fluid-type relation one end of a hollow right angle elbow 215 and 217, respectively. The vacuum generated at source 36 is communicated along a conduit 219 to the interior of the elbow 217 and thence to the interior of the air-tight bucket 203. See FIG. 11. The vacuum pressure is communicated from the interior of the bucket through the hollow of the elbow 215 along the hollow coupling 218 and the hollow fitting 220 to a flexible tube 222 formed of suitable synthetic resinous material. The vacuum vents through the hollow of a distal probe, generally designated 224, at ports 226 and 294 located at the distal end or tip 228 of the probe. See FIG. 12.

Adjacent the fitting 220 is disposed a probe storage device, generally designated 230, for holding the probe 224 when not in use. The probe storage device 230 comprises a support sleeve 232 comprising rounded fore and aft ends 234 and 236. Otherwise, the sleeve 232 is illustrated as being solid and of uniform thickness throughout, comprising an exterior annular surface 238 and an interior annular surface 240. The diameter of the surface 240 is selected to be substantially the same as the outside diameter of the catheter tube 220 so as to form a tight fit between the collar and the tube. This tight fit may be overcome by manual force so that the sleeve 232 may be located at any desired position along the length of the tube 222, where ever storage of the probe 224 during nonuse would be most appropriate for the preferences of the attending nurse.

The probe storage device 230 also comprises a funnel-shaped probe storage receptacle 242. Probe receptacle 242 comprises a closed bottom end 244 and an upwardly directed annular wall 246, illustrated as being of uniform thickness throughout and comprising exterior annular wall surface 248 and interior annular wall surface 250. The axial length of the wall 246 is selected so as to be greater than the length of the tip 228 of the probe 224 adapted to be received within the hollow chamber 252 formed by the wall surface 250. See FIG. 10. The probe storage member 242 is preferably formed of flexible synthetic material which is shape-retaining as one piece using a single shot injection molding technique of conventional type. Thus, cylindrical wall 246 is integral with the closed bottom wall 244 and integrally emerges with a frusto-conical top wall 254. Frusto-conical wall 254 terminates in a beveled upper horizontal edge 256, is illustrated as being of uniform thickness throughout and comprises interior and exterior wall surfaces 258 and 259. The conical configuration of the wall 254 is selected to make entry by the tip 228 easy and to match the external configuration of the probe to accommodate nesting of the probe in the storage member 242, as illustrated in FIG. 10, during intervals of nonuse.

A pair of spaced parallel cantilevered beams 260, integral with the sleeve 232 and the cylindrical wall 246 of the probe storage member 242 provide sufficient structural support to hold both the probe and the receiving member 242 in an erect condition during storage. Preferably, the probe storage device 230 is formed as one piece from rigid synthetic resinous material of a suitable type using a single shot injection molding technique.

In reference to FIG. 10, the probe 224 itself is illustrated as comprising an elongated sleeve 270 which comprises a wall 274, the exterior surface 272 of which is longitudinally serrated. The wall 274 also comprises an internal annular surface 276. The end 278 of the tube 222 is fitted into and secured at the trailing end of the surface 276, using a suitable bonding agent or adhesive. The wall 276 defines a chamber 280 which is in fluid communication with the interior of the tube 222.

The thickness of the wall 274 is enlarged at site 282 adjacent diagonal internal shoulder 284, which reduces the diameter of the internal vacuum chamber at site 286. The exterior diameter of the probe is also reduced at diagonal internal shoulder 288, which integrally merges with the exterior surface 290 of the probe tip 228. The tip 228 is illustrated as being equipped with two opposed side ports 226. A third axial port 294 also exists at the end of the central passageway through the probe. The lower edge 296 of the tip 228 is illustrated as being rounded.

With the vacuum source 36 (FIG. 11) operating, negative pressure is delivered to the interior of the sealed bucket 203 and along the hollow interior passageway of tube 222 and the hollow chambers 280 and 286 of the probe 224. The probe 224, removed from its storage device 242 by the user of the system, is placed manually in alignment with the probe-receiving assembly 100, as illustrated in FIG. 11. When the tip 228 of the probe is inserted into the interior probe-receiving member 104, it assumes the position illustrated in FIG. 12. The end edge 296 of the probe tip 228 engages wall 150 and stretches or elongates the member 104 until the wall 150 is below and no longer sealed to the collar 106. See FIG. 7. Thus, the negative pressure contained within the hollow interior of the probe 224 is transmitted first to the open chamber 160 and thence across slots 168 to the interior of the associated sealed container 90 via the siphon pipe 108. This then causes the liquid accumulated in the reservoir 96 to be evacuated by suction up the evacuation tube 108, along a portion of the collar 106, through chamber 160 of member 104 into the chamber 160 and thence through the probe ports 226 into the interior 286, 280 of the probe 224, along the hollow passageway of the tube 222 and into the sealed storage bucket 203. See FIG. 12.

The nature of the probe-receiving assembly 100, and particularly the requirement that member 104 be stretched by the probe, is that the user of the probe 224 must manually hold the probe in the inserted position illustrated in FIG. 12 in order to cause vacuum evacuation of liquid contained in the receptacle 96 to continue. If the user, for whatever reason, removes the manual force needed to hold the probe in the evacuating position, the memory of the material from which member 104 is formed causes the probe to migrate from the inserted position of FIG. 12 to the removed position shown in FIG. 11.

Reference is now made to FIGS. 13 and 14, which illustrate an additional presently preferred embodiment, generally designated 300. Drain system 300 is illustrated as comprising two containers 90', connected, respectively, to ventilating tubes 54' and 56'. Tubing 54' is severed at ends 302 and tubing 56' likewise severed at end edges 304. The ends of the tubing sections 54' and 56' are illustrated as being force-fit upon opposed arms of T-shaped fittings 306, which accommodate displacement along the tubing sections 54' and 56' of the ventilating gas as well as drainage accumulating therein into the associated liquid-accumulating container 90'. Each container 90' comprises a press-fit lid 92' and a lower elongated receptacle 94'. Each receptacle 94' comprises an open top covered by the associated lid 92' in fluid-tight relation, a frusto-conical site wall 308 illustrated as having a uniform wall thickness and taper throughout. The side wall 308 merges at annular site 310 with a tapered bottom surface 312, the central annular portion of which integrally merges with a downwardly directed tubular fitting 314. This merger occurs at site 316.

Each container 90' comprises an internal float mechanism comprising a cylindrical housing, generally designated 318. Cylindrical housing 318 comprises a vertically directed cylindrical wall 320 illustrated as being of uniform thickness throughout and comprising outside annular surface 322 and inside cylindrical surface 324. Wall 320, at the top edge thereof merges with an inwardly directed lip 326, which comprises a top surface 328 and a bottom surface 330. An aperture 332 is centrally defined by the lip 326.

The wall 320 integrally merges with the wall 312 at site 316.

Within the cylindrical wall 320 is a float valve mechanism comprising a float ball valve 336, formed of buoyant synthetic resinous material. As liquid 340 accumulates in container 94', the float ball 336 is elevated as the surface of the water elevates (until contact is made with the wall 326). Such lifting of the ball 336 creates liquid communication between the interior of the wall 308 and the interior of the cylindrical wall 320 through apertures 342 and from thence through the hollow fitting 314 and the fluid-tight liquid evacuation tube 344.

To the contrary, when liquid is evacuated from the interior of container 94', the level of liquid 340 falls until the ball 336 is seated upon the top surface of an O-ring 346 thereby terminating any further flow of liquid into the interiors of the fitting 314 and the tubing 344.

Returning to FIG. 13, liquid evacuation tubing 344 is coupled in fluid-tight relation to sleeve 350 which in turn is connected to one end 352 of a normally closed manually actuated vacuum valve 354. It is presently preferred that the valve 354 be the same as a normally closed manually operable valve disclosed in U.S. Pat. No. 4,569,344, the contents of which are incorporated herein by reference. The other end 356 of the valve 354 is connected in liquid-tight relation via sleeve 358 to a tube 360, which is subjected to negative or vacuum pressure, as illustrated by arrow 362.

Thus, when the nurse or medical technician depresses the actuator of the valve 354, the vacuum present in tube 360 is communicated across the valve 354, along the tubing 344 to the container 94'. This is done at a point in time when substantial liquid has accumulated in the reservoir 94', which is preferably transparent or translucent so that a medical attendant can visually observe the amount of liquid accumulation at any point in time. With a substantial liquid accumulation present in receptacle 94', the float ball 336 will be in an elevated position well above the O-ring 346. Thus, the negative pressure communicated, as mentioned above, across valve 354 will be applied to the liquid within the receptacle 94', drawing the same from the receptacle. When the liquid has been essentially removed from the receptacle 94', the ball 336 seats once more upon the O-ring 346, terminal&ing delivery of negative pressure to the interior of the receptacle 94'. The nurse or other medical attendant releases the actuator of the valve 354 at this point in time, which closes the valve 354 and completes the liquid removal cycle. Liquid so removed may be disposed of in any suitable fashion, use of a closed container such as container 203, previously described, being presently preferred so as to retain the system in a closed condition and prevent contamination.

The invention may be embodied in other specific forms without department from the spirit or essential characteristics thereof. The present embodiments, are, therefore, to be considered in all respects as illustrative and not restrictive, the scope of the invention being indicated by the appended claims rather than by the foregoing description, and all changes which come within the meaning and range of equivalence of the claims are therefore to be embraced therein.

What is claimed and desired to be secured by United States Letters Patent is:

1. A closed ventilating/drainage system for involuntary respiration of a medical patient comprising:
   ventilating tubing comprising fluid flow passageway means by which influent and effluent ventilating gas is delivered to and received from a medical patient whereby liquid accumulates in the tubing;
   liquid drainage means disposed at a low point along the tubing in fluid communication with the fluid flow passageway means, the drainage means comprising hollow fluid flow path means along which ventilating gas and liquid accumulated in the tubing respectively pass, the drainage means further comprising a fluid-tight internally hollow liquid storage container means closed to the atmosphere and contamination therefrom, said container means being disposed below the fluid flow path means and non-gravity hollow drainage means closed to the atmosphere and contamination therefrom, the interior of which is interposed in fluid communication with the hollow of the liquid storage container means and normally-closed manually operated suction means whereby liquid passing along the fluid flow path means drains by force of gravity into the hollow of the liquid storage container means and is selectively evacuated from the container means via the hollow drainage means and the suction means without removal of the container means from the system and without termination of ventilation, said hollow drainage means further comprising a normally-closed vacuum probe-receiving valve means and at least one openable valve site and wherein the suction means comprises a vacuum probe which is manually inserted into the valve means to open the valve site and by which negative pressure provided by the probe is selectively communicated to the hollow interior of the liquid storage container means across the open valve site to evacuate liquid stored in the container means through the manually inserted probe.

2. A ventilating system according to claim 1 wherein the ventilating tubing comprises at least two spaced tubes.

3. A closed drainage system for manually removing interior liquid from within an involuntary respirator tubing, the drainage system comprising:
  hollow fluid-tight liquid storage reservoir means closed to the atmosphere and contamination therefrom;
  hollow fluid flow means comprising first means in liquid flow communication with hollow of the reservoir means and second means by which the interior liquid in the respiration system is placed in unimpeded gravity flow relationship with the first means;
  non-gravity liquid aspirating means comprising normally-closed valve means associated with the reservoir means by which vacuum pressure is manually caused to be selectively applied directly to the hollow of the reservoir means to remove liquid therefrom without separation of the reservoir means from the system,
  said liquid aspirating means comprise a vacuum probe-receiving chamber means comprising said normally-closed valve means and further comprising a portable vacuum probe by which suction is manually caused to be selectively communicated directly to the hollow of the reservoir means.

4. A drainage system according to claim 3 wherein the liquid aspirating means comprise a vacuum probe-receiving elongatable chamber means comprising said normally-closed valve means and further comprising a portable vacuum probe by which the normally-closed valve means are opened by elongation of the chamber means caused by manual advancement of the probe therein to communicate the vacuum of the probe directly to the hollow of the reservoir means.

5. A drainage system according to claim 4 wherein the chamber means comprise a material with memory and the vacuum probe, when inserted is biased by the elongated chamber means away from the position which opens the normally-closed valve means requiring the probe to be manually held in the elongated chamber means for the normally-closed valve means to be in its open condition.

6. A drainage system according to claim 4 wherein a suction tube is interposed between the interior bottom of the reservoir means and the chamber means.

7. A drainage system according to claim 3 wherein the normally-closed valve means comprise exposed manual actuator means by which the normally-closed valve means are manually opened and manually held open accommodating communication of vacuum pressure to the hollow of the reservoir means.

8. A closed drainage system for manually removing interior liquid from within respirator tubing without interruption of ventilation, the drainage system comprising:
  hollow first fluid-tight liquid storage reservoir means closed to the atmosphere and contamination therefrom;
  hollow fluid flow means comprising means in liquid flow communication with the hollow of the first reservoir means and means by which the interior liquid in the respiration system is placed in unimpeded gravity flow relationship with the liquid flow communication means;
  non-gravity liquid aspirating means comprising normally-closed valve means associated with the first reservoir means by which negative pressure from a vacuum source is manually caused to be selectively applied directly to the hollow of the first reservoir to remove liquid therefrom without separation of the first reservoir means from the system;
  hollow fluid-tight second liquid storage reservoir means interposed in selective fluid communication between the first reservoir means and the source of vacuum pressure whereby said application of vacuum pressure directly to the hollow of the first reservoir means causes liquid in the first reservoir means to be evacuated to the second reservoir means.

9. A drainage system according to claim 8 wherein the liquid aspirating means comprise vacuum probe-receiving chamber means and comprising a portable vacuum probe for manual placement in the chamber means.

10. A drainage system according to claim 8 wherein the liquid aspirating means comprise normally closed valve means and exposed manual valve actuator means by which the valve means are manually opened and manually held open accommodating communication of vacuum pressure directly to the hollow of the first reservoir means.

11. A method of draining moisture from a closed ventilating system attached to a medical patient without interruption of patient ventilation comprising the steps of:
  gravity-directing liquid contained in a pressurized ventilating system to a low point in the system;
  gravity-displacing liquid arriving at said low point from the ventilating system to a hollow interior of an fluid-tight liquid storage container closed to the atmosphere and contamination therefrom, the hollow interior of the container being subject to the pressure of the ventilating system;
  periodically aspirating the accumulated liquid from the liquid storage container across a manually operated normally closed suction valve by a nagative pressure applied across the suction valve directly to the interior of the container.

* * * * *